United States Patent
Hares

(10) Patent No.: US 11,771,302 B2
(45) Date of Patent: Oct. 3, 2023

(54) IMAGE CORRECTION OF A SURGICAL ENDOSCOPE VIDEO STREAM

(71) Applicant: CMR SURGICAL LIMITED, Cambridge (GB)

(72) Inventor: Luke David Ronald Hares, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 252 days.

(21) Appl. No.: 17/270,239

(22) PCT Filed: Aug. 23, 2019

(86) PCT No.: PCT/GB2019/052366
§ 371 (c)(1),
(2) Date: Feb. 22, 2021

(87) PCT Pub. No.: WO2020/039202
PCT Pub. Date: Feb. 27, 2020

(65) Prior Publication Data
US 2021/0327037 A1    Oct. 21, 2021

(30) Foreign Application Priority Data
Aug. 24, 2018 (GB) ...................... 1813877

(51) Int. Cl.
*G06T 5/00* (2006.01)
*A61B 1/00* (2006.01)
(Continued)

(52) U.S. Cl.
CPC ........ *A61B 1/000095* (2022.02); *A61B 34/30* (2016.02); *G06T 5/008* (2013.01);
(Continued)

(58) Field of Classification Search
CPC . A61B 34/30; A61B 90/361; A61B 1/000095; A61B 2034/301;
(Continued)

(56) References Cited

U.S. PATENT DOCUMENTS

2003/0095707 A1* 5/2003 Colmenarez ............ G06T 7/246
382/173
2006/0258938 A1* 11/2006 Hoffman ............ A61B 1/00194
600/424
(Continued)

FOREIGN PATENT DOCUMENTS

CN    102622768 A    8/2012
JP    2006007289 A   1/2006
(Continued)

OTHER PUBLICATIONS

Peters, Brian S., et al. "Review of emerging surgical robotic technology." Surgical endoscopy 32 (2018): 1636-1655.*
(Continued)

*Primary Examiner* — Li Liu
(74) *Attorney, Agent, or Firm* — Lando & Anastasi, LLP

(57) ABSTRACT

A method of real-time image correction of a video stream from a surgical endoscope of a surgical robotic system. The video stream comprises a sequence of images. The method comprises: for an image in the sequence of images, identifying a plurality of regions, each region having a different range of values of at least one image property to another region; applying a mask to the image which applies a region-specific modification to each region, each region-specific modification modifying the at least one image property of that region; deriving data from the surgical robotic system; determining a relationship between features in the image from the derived data; modifying the mask for a predicted relationship between the features at the time of
(Continued)

a subsequent image in the video stream; and applying the modified mask to the subsequent image in the video stream.

17 Claims, 4 Drawing Sheets

(51) Int. Cl.
A61B 34/30 (2016.01)
G06T 7/579 (2017.01)
G06T 7/11 (2017.01)
G06T 7/174 (2017.01)
G06T 5/50 (2006.01)

(52) U.S. Cl.
CPC ............... G06T 5/009 (2013.01); G06T 5/50 (2013.01); G06T 7/11 (2017.01); G06T 7/174 (2017.01); G06T 7/579 (2017.01); A61B 2034/301 (2016.02); G06T 2207/10016 (2013.01); G06T 2207/10024 (2013.01); G06T 2207/10028 (2013.01); G06T 2207/10068 (2013.01); G06T 2207/20208 (2013.01); G06T 2207/30004 (2013.01)

(58) Field of Classification Search
CPC ........ A61B 1/00009; A61B 2034/2065; A61B 17/00234; A61B 90/37; G06T 2207/10068; G06T 2207/10016; G06T 5/008; G06T 5/40; G06T 7/11; G06T 5/001; G06T 7/70
See application file for complete search history.

(56) References Cited

U.S. PATENT DOCUMENTS

| 2008/0298685 | A1 | 12/2008 | Maeda |
| 2009/0129675 | A1* | 5/2009 | Eggert .................. G06T 7/215 |
| | | | 382/173 |
| 2014/0194896 | A1* | 7/2014 | Frimer ............... A61B 1/00149 |
| | | | 606/130 |
| 2015/0223725 | A1 | 8/2015 | Engel et al. |
| 2017/0046836 | A1* | 2/2017 | Bramwell ............... G06T 5/007 |
| 2017/0084027 | A1 | 3/2017 | Mintz et al. |
| 2018/0271615 | A1* | 9/2018 | Mahadik ................ A61B 90/37 |
| 2019/0122345 | A1 | 4/2019 | Kamio et al. |

FOREIGN PATENT DOCUMENTS

| JP | 2012152266 A | 8/2012 |
| JP | 2015008785 A | 1/2015 |
| WO | 2015162409 A1 | 10/2015 |
| WO | 2016162925 A1 | 10/2016 |
| WO | 2016199273 A1 | 12/2016 |
| WO | 2017175452 A1 | 10/2017 |
| WO | 2018140788 A1 | 8/2018 |

OTHER PUBLICATIONS

Ott, Laurent, et al. "Robotic assistance to flexible endoscopy by physiological-motion tracking." IEEE Transactions on Robotics 27.2 (2011): 346-359.*
Japanese Notification of Reasons for Refusal from corresponding Japanese Application No. 2021-507783 dated Jul. 26, 2022.
Japanese Notification of Reasons for Refusal from corresponding Japanese Application No. 2021-057783 dated Mar. 15, 2022.
Notification of Transmittal of the International Search Report and the Written Opinion of the International Searching Authority from corresponding PCT/GB2019/052366 dated Jan. 28, 2020.
United Kingdom Search Report from corresponding United Kingdom Application No. GB1813877.6 dated Feb. 25, 2019.
Japanese Reconsideration Report by Examiner before Appeal from corresponding Japanese Application No. 2021-507783 dated Jun. 27, 2023.
Takematsu et al., "Improving image quality of photographic images using Retinex based on statistical evaluation of mage quality", Journal of Japan Photography Society, Aug. 25, vol. 67, No. 4, 2004, pp. 410 to 416 [English Abstract only—on pp. 2-3].

* cited by examiner

IMAGE CORRECTION OF A SURGICAL ENDOSCOPE VIDEO STREAM

CROSS-REFERENCE TO RELATED APPLICATIONS

This application is a U.S. National Phase Application under 35 U.S.C. § 371 of International Application No. PCT/GB2019/052366, filed Aug. 23, 2019, which claims priority to United Kingdom Application No. 1813877.6, filed Aug. 24, 2018. Each application referenced above is hereby incorporated by reference in its entirety for all purposes.

BACKGROUND

This disclosure relates to image correction of the video stream from a surgical endoscope of a surgical robotic system.

In minimally invasive surgery, the surgical site is imaged via a surgical endoscope. The endoscope is a camera which typically has a tip comprising a light source for illuminating the site and one or more lenses for acquiring the video stream. The video stream is displayed in real time on a display enabling the surgeon to view the surgical site and the surgical instruments he is manipulating.

In order to sufficiently illuminate the surgical site, the light source on the endoscope is very intense. In the resulting video stream, the illuminated area is in high contrast to the remainder of the image which is in shadow. In minimally invasive surgery the endoscope has a very narrow diameter, thus the light source is very close to the optical axis of the endoscope. Tissue is wet and shiny, and hence causes a strong reflection back into the lens when illuminated, which is exacerbated when the tissue is near the optical axis and close to the endoscope. This overly bright portion of the image is in stark contrast to the periphery of the image which appears very dark. Tissue which is further away from the endoscope also appears very dark. Consequently, the surgeon is left with a poor view of the surgical site with limited visibility.

It is known to apply a transform to the video stream from the endoscope to improve the quality of the images viewed by the surgeon. Brightness and contrast are adjusted to make the central area of the image more visible. However, because other areas of the image are much darker than the central area, when the transform is applied uniformly across the image, it further degrades the visibility of those darker areas.

It is known to apply a different transform to the central area of the image from the endoscope than to the periphery of the image, for example to darken the central area and brighten the periphery. Whilst an improvement to uniformly applying a transform across the whole image, this approach suffers from the problem that it does not improve the visibility of high contrast regions within the central area or within the periphery.

More sophisticated techniques for processing still images are known, which involve manual manipulation of the images. Techniques involving manual manipulation are not suitable for real-time correction of a video stream from an endoscope as is required in this field to enable the surgeon to better view the surgical site he is operating in.

There is a need for an improved method of image correction of a video stream from a surgical endoscope in real-time so as to improve the visibility across the whole image to the surgeon operating at the surgical site.

SUMMARY OF THE INVENTION

According to a first aspect, there is provided a method of real-time image correction of a video stream from a surgical endoscope of a surgical robotic system, the video stream comprising a sequence of images, the method comprising: for an image in the sequence of images, identifying a plurality of regions, each region having a different range of values of at least one image property to another region; applying a mask to the image which applies a region-specific modification to each region, each region-specific modification modifying the at least one image property of that region; deriving data from the surgical robotic system; determining a relationship between features in the image from the derived data; modifying the mask for a predicted relationship between the features at the time of a subsequent image in the video stream; and applying the modified mask to the subsequent image in the video stream.

The method may further comprise storing a set of predetermined modifications, and generating each region-specific modification as a weighted combination of two or more predetermined modifications.

The predetermined modifications may modify one or more of the following image properties: brightness, contrast, gamma and colour.

The predicted relationship between the features at the time of the subsequent image may be such that the shape of one or more of the features in the image has changed, or that the relative positions of the features have changed.

The data may comprise the position of the surgical endoscope relative to another feature in the image.

The data may comprise depth information of the features in the image. The depth information may be derived from movement of the surgical endoscope. The video stream may be a combination of two stereo video channels of the surgical endoscope, and the method may comprise deriving the depth information from the two stereo video channels of the surgical endoscope.

The data may comprise identification of features in the image.

The method may comprise selecting regions of the image to correspond to identified features of the image, and applying feature-specific modifications to those selected regions.

The method may comprise tracking the surgeon's focus, selecting a first region of the image to be centred on the surgeon's focus, selecting a second region of the image to exclude the surgeon's focus, and applying different region-specific modifications to the first and second regions.

The method may comprise identifying a plurality of regions of the subsequent image based on the predicted relationship between the features at the time of the subsequent image in the video stream, wherein applying the modified mask to the subsequent image in the video stream comprises applying a region-specific modification to each region of the subsequent image.

The method may further comprise applying an iteratively updated mask to further images of the video stream by: deriving further data from the surgical robotic system; determining an updated relationship between features in a further image of the sequence of images from the derived further data; further modifying the mask to form an updated mask for the updated predicted relationship between the features at the time of a yet further image in the video stream; applying the updated mask to the yet further image in the video stream; and iteratively performing the above steps for further images of the video stream.

The mask may be updated at a slower rate than the image frame rate of the video stream. The mask may only be updated upon gross changes of the features in the image. The mask may only be updated upon gross movement of the surgical endoscope and/or the patient the surgical endoscope is inside.

BRIEF DESCRIPTION OF THE DRAWINGS

The present disclosure will now be described by way of example with reference to the accompanying drawings. In the drawings.

DETAILED DESCRIPTION

Figure 1:
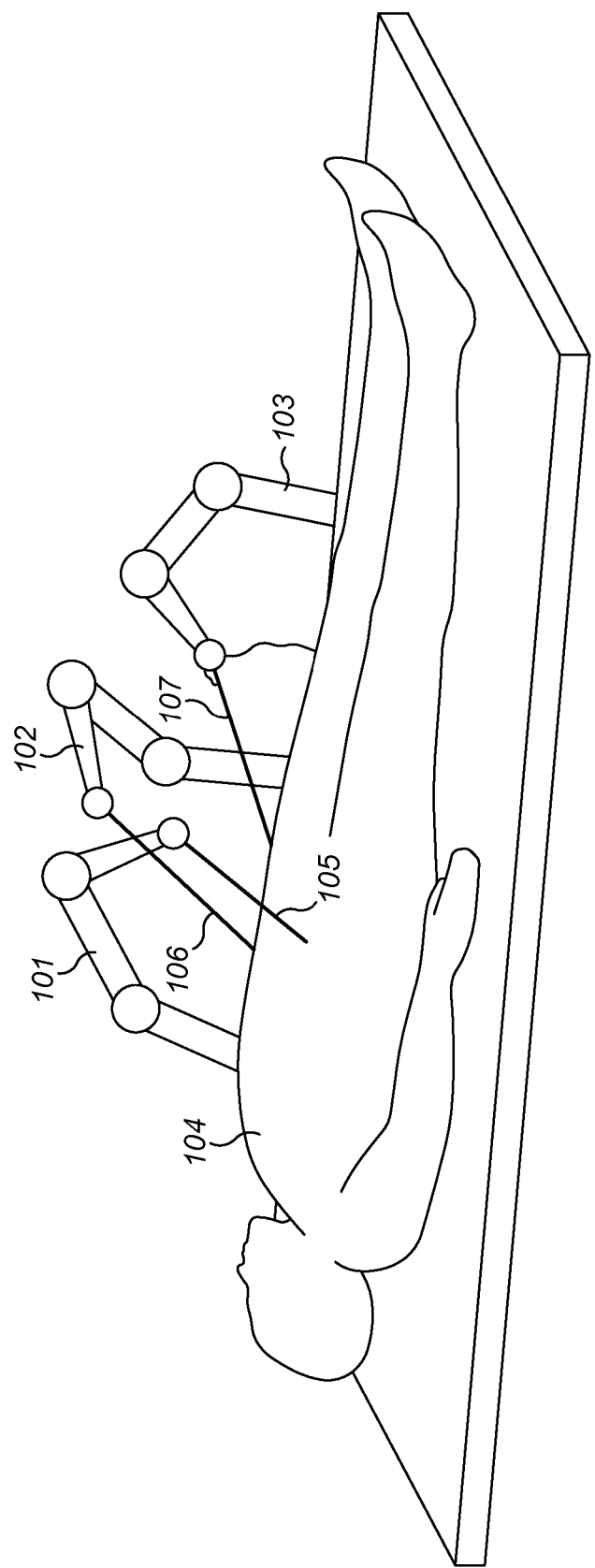
FIG. 1 illustrates a person being operated on by a set of surgical robots.
Figure 2:
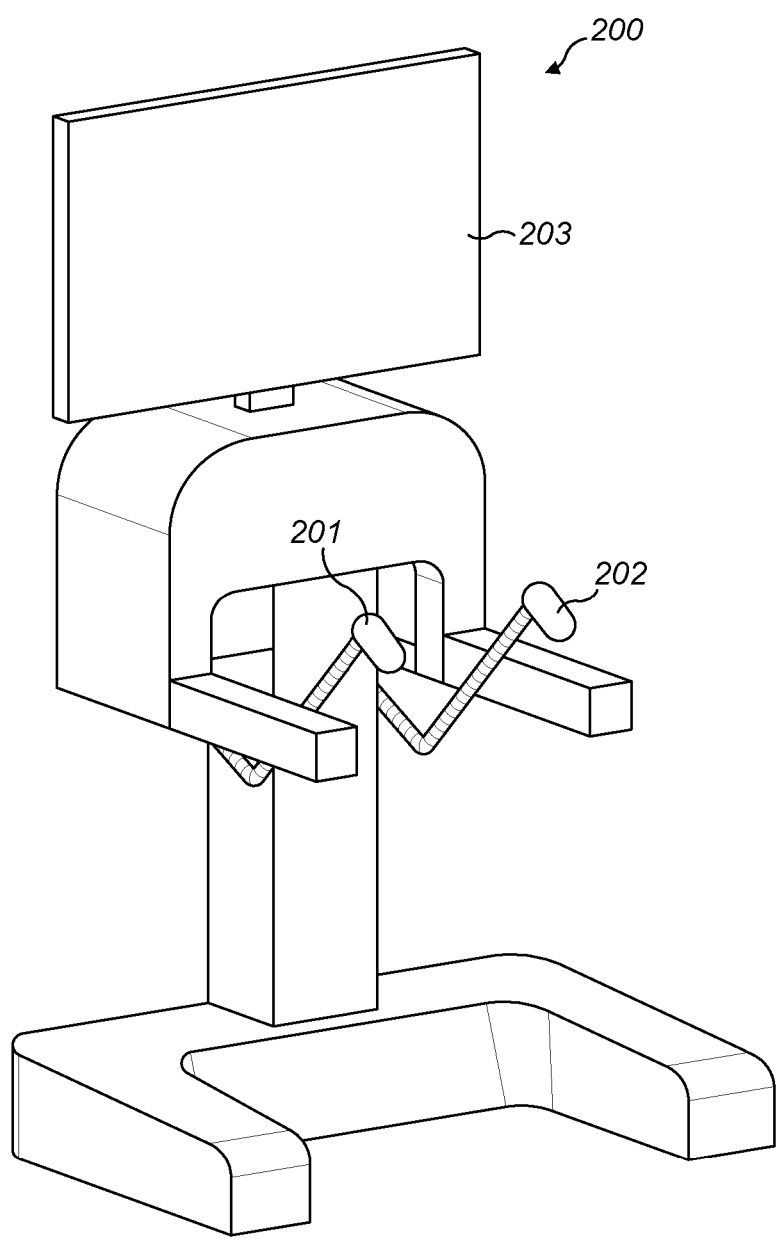
FIG. 2 illustrates a surgeon console.

FIG. 1 illustrates surgical robots 101, 102, 103 performing an operation on a person 104. Each robot comprises an articulated arm connected to a base. Each of robots 101 and 102 has a surgical instrument 105, 106 connected to the end of its arm. A surgical endoscope 107 is connected to the arm of robot 103. The surgical instruments 105, 106 and surgical endoscope 107 each access the surgical site through an incision in the body 104. A surgeon controls the surgical instruments, and optionally the surgical endoscope, from a surgeon console 200, shown in FIG. 2. The surgeon manipulates hand controllers 201, 202. A control system converts the movement of the hand controllers into control signals to move the arm joints and/or instrument end effector of one of the surgical robots. The video feed from the surgical endoscope 107 at the surgical site is displayed on display 203. The surgeon is thereby able to view the surgical site including the instrument end effector that he is manipulating with the hand controllers 201, 202.

Figure 3:
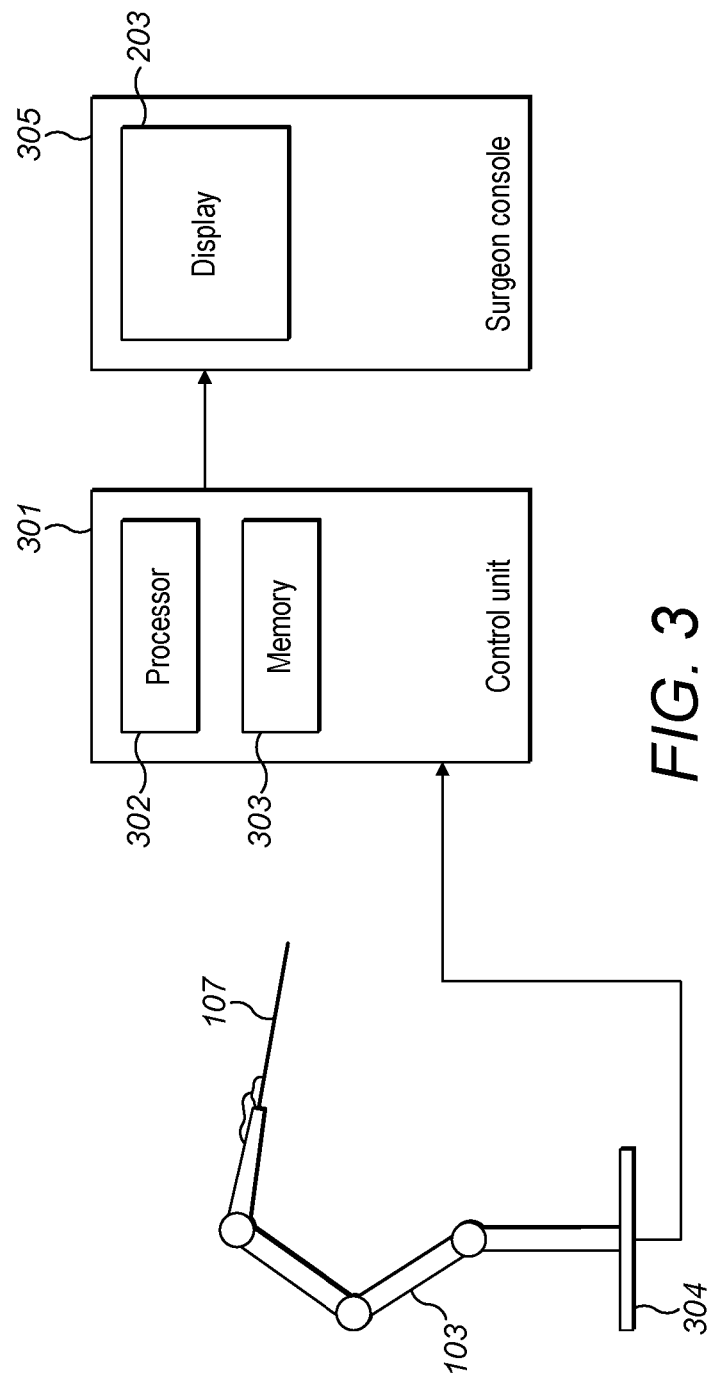
FIG. 3 illustrates a schematic diagram of the portion of a surgical robotic system relating to a surgical endoscope.

FIG. 3 illustrates the portion of the surgical robotic system relating to the surgical endoscope 107. The surgical endoscope 107 is attached to the end of robot arm 103 that is distal from its base 304. The video stream from the surgical endoscope is received by control unit 301 where it is processed and then output to the surgeon console 305 where it is displayed on display 203. The control unit 301 comprises a processor 302 and a memory 303. The memory stores, in a non-transient way, software code that can be executed by the processor to cause the processor to correct the video stream from the surgical endoscope 107 in real-time in the manner described herein. Control unit 301 is shown as being remote from both the surgeon console 305 and the surgical robot 103. Alternatively, the control unit 301 may be incorporated within the surgeon console 305. As a further alternative, the control unit 301 may be incorporated within surgical robot 103 or another surgical robot of the surgical robotic system.

The processor 302 performs real-time image correction of the video stream from the surgical endoscope 107 in accordance with the following exemplary methods described with reference to FIG. 4.

Figure 4:
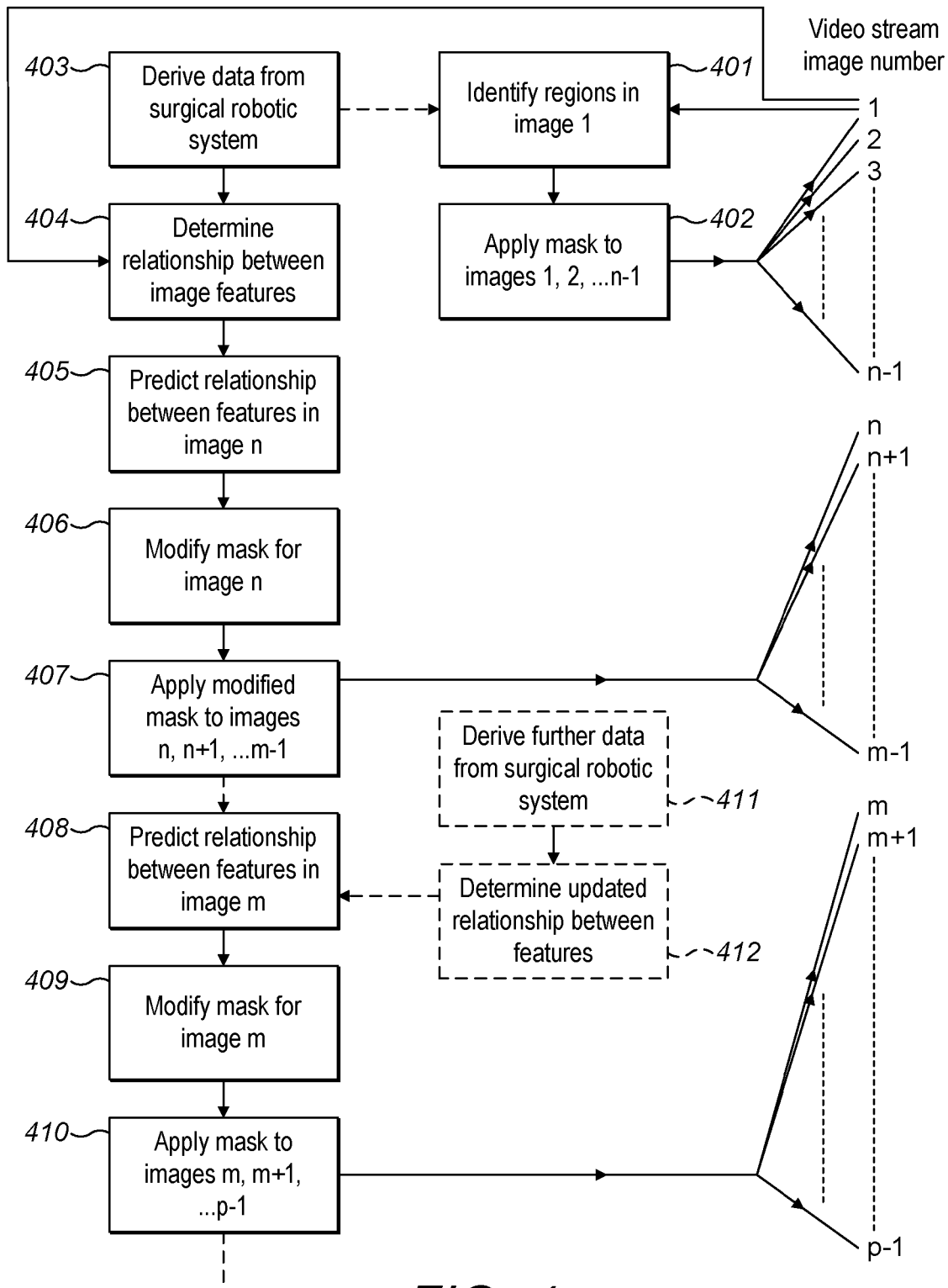
FIG. 4 illustrates a flowchart showing the process of image correction of a video stream from a surgical endoscope.

The video stream comprises a sequence of images, numbered 1, 2, 3, . . . , n−1, n, n+1, . . . , m−1, m, m+1, . . . , p−1, p, . . . in FIG. 4. The processor processes each image of the sequence of images. At step 401, the processor identifies a plurality of regions in image 1. Each region consists of one or more pixel. Each region is distinguished from another region by having a different range of values of at least one image property. The image properties of a region include brightness, contrast, gamma and colour. Any one or more of these image properties may be different in different regions. At step 402, the processor applies a mask to image 1. The mask applies a region-specific modification to each region of the image. The region-specific modification of one region is different to the region-specific modification of another region. Each region-specific modification modifies at least one image property of that region. In the case that the regions are identified on the basis that they have a different range of values of a particular image property, for example brightness, then the region-specific modification would modify that particular image property. The region-specific modification may also modify other image properties of the region. The processor applies the same mask to a series of images. For example, the processor applies the mask created on the basis of image 1 to images 1, 2, . . . , n−1.

At step 403, the processor derives data from the surgical robotic system of which the surgical endoscope is a part. Example data which may be derived is described below. At step 404, the processor uses the derived data to determine a relationship between features in image 1. These features may, for example, be organs, tissue structures and/or surgical instruments. At step 405, the processor uses the determined relationship between the features in image 1 to predict a relationship between those same features at the time of a subsequent image in the image sequence. In FIG. 4, this subsequent image is image n. At step 406, the processor then modifies the mask generated for image 1 for the predicted relationship between the features at the time of image n. At step 407, the processor applies the modified mask to image n. The processor applies the same mask to a series of images. In the case of FIG. 4, the processor applies the modified mask to images n, n+1, . . . , m−1.

The processor performs an iterative process in which the mask is updated and applied to a series of images, and then the mask is updated again and applied to a further series of images, and so on until the end of the video stream. In order to update the mask for each further image, the relationship between the features in that further image is predicted. In FIG. 4, the next image that the mask is updated for is image m. At step 408, the processor predicts the relationship between the features in image m. This prediction may be based on the data derived from the surgical robotic system in step 403 in the same manner that the prediction was made for image n in step 405. Alternatively, or in addition, the prediction may be based on further data derived from the surgical robotic system at step 411. At step 412, this further derived data is used to determine an updated relationship between the features at the time the further data is derived. In this case, at step 408, the processor predicts the relationship between the features at the time of image m based on the updated relationship between the features in step 412. At step 409, the mask is modified to form an updated mask for the updated predicted relationship between the features at the time of image m. At step 410, the updated mask is applied to image m. The processor applies the same mask to a series of images. In the case of FIG. 4, the processor applies the updated mask to images m, m+1, p−1. The processor then generates a further updated mask for a series of images starting with image p using the same process described above with respect to image m. The process continues iteratively until the video stream stops.

The data that is derived from the surgical robotic system at steps 403 and 411 may include data which enables the position and/or relative movement of features in the image to be determined. For example, it may be determined from force feedback or visual analysis of the image that a surgical instrument is touching a tissue structure or organ. The relative positions of the surgical instrument and surgical endoscope can be calculated from: (i) the known relative locations of the bases of the surgical robot arms which support the instrument and endoscope; (ii) the position of the surgical instrument relative to its supporting robot arm which can be calculated using forward kinematics from the joint positions of the robot arm sensed by position sensors on those joints; and (iii) the position of the surgical endoscope relative to its supporting robot arm which can be calculated using forward kinematics from the joint positions of the robot arm sensed by position sensors on those joints. Thus, the position of the surgical endoscope relative to the surgical instrument and the tissue structure/organ is known. Data relating to movement of one or more of the surgical instrument, surgical endoscope and patient may also be derived from the surgical robotic system. For example, the command signals sent from the surgeon's hand controllers to manipulate the surgical instrument specify the movement of the robot arm holding the surgical instrument and movement of the articulations of the surgical instrument in order to carry out the commanded manipulation. From the initial relationship between the features in the image and the data relating to the subsequent movement of the surgical instrument, surgical endoscope or patient, the processor is able to predict the relationship between the features at a specified time in the future. The processor thus modifies the mask to account for the change in the relative positions of the features in the image at that specified time in the future, and applies the modified mask to an image at that specified future time in the video stream.

The data that is derived from the surgical robotic system at steps 403 and 411 may include data which enables the arrangement of features in the image to be deduced. Specifically, the data may enable the depth of features in the image to be deduced. This data may be the movement of the surgical endoscope. The command signals driving the movement of the surgical endoscope specify movement of the robot arm holding the surgical endoscope and movement of the articulations of the surgical endoscope in order to carry out the commanded movement. The distance and direction that the surgical endoscope moves can be deduced from these command signals. Hence, the distance and direction that the camera at the tip of the surgical endoscope, and hence the image, moves can be deduced. The change in the features of the image as the endoscope moves enables depth information about those features to be determined. For example, if the endoscope moves past a feature, then the dimension of that feature in the direction of travel of the endoscope may be estimated. As another example, if the endoscope moves towards a distal feature, then the change in size of that feature may be used to estimate how far away the feature is.

Data relating to the depth of features in the image may be deduced from the video stream itself. The endoscope may have two stereo video channels. The two channels are offset, thus rendering a 3D view of the surgical site on the display. The processor can estimate the dimensions and relative depths of the features in the image from this 3D view.

From the initial relationship of the features and the depth data, the processor is able to predict the relationship between the features at a future time following movement of the surgical endoscope. The processor thus modifies the mask to account for the change in the relative positions of the features in the image at that future time, and applies the modified mask to an image at that future time in the video stream.

The data that is derived from the surgical robotic system at steps 403 and 411 may include data which identifies features in the image. For example, organs and/or tissue structures at the surgical site may be tagged. This tagging may be done by the surgeon, by other member of the operating room staff, or by automatic detection by the control unit 301. Once tagged, an organ or tissue structure can then be tracked kinematically through the video stream from one image to another by the processor. The processor may select the organ/tissue structure to be a region, and apply an organ/tissue structure specific mask to the organ/tissue structure. For example, the processor may store a defined mask for a kidney, and having identified a kidney, apply the kidney specific mask to the kidney.

The relationship between features in the image which is determined from the data derived from the surgical robotic system may comprise the arrangement of features in the image and/or the relative positions of features in the image. This relationship may change over time as a result of the shape of one or more of the features in the image changing. If the feature has been identified, then its movement and/or change in shape over time may be anticipated. For example, the shape of a feature in the image may change/deform as a result of the feature physically changing shape due to a physiological process in the body. For example, an artery pulses over time as a result of the patient's heartbeat, and the diaphragm moves up and down as a result of the patient breathing. The shape of the feature in the image may change as a result of the surgical endoscope moving past the feature, and hence the feature being viewed from a different angle. The shape of the feature in the image may change as a result of it being manipulated by a surgical instrument.

As described above, the mask applies a region-specific modification to each region of the image. The mask modifies one or more image property of the region. These image properties include brightness, contrast, gamma and colour. As a simple example, the processor may identify three regions in an image. The first region is too dark, the second region is too bright, and the third region is an acceptable brightness. The mask the processor applies to the image comprises region-specific modifications which increase the brightness of the first region, decrease the brightness of the second region, and not alter the brightness of the third region. The resulting image has a more even contrast across it which improves the visibility of the image to the surgeon.

The operative site generally has little variation in colour. Mostly, it is different shades of red with some areas which appear whiter. The processor may generate a mask to apply false colours to the image to increase the visibility of features within the image. For example, a region-specific modification may include a fluorescence colour channel to be superimposed on the region.

The control unit 301 may store a set of predetermined modifications in memory 303. The processor then applies one or more of these predetermined modifications to each region. In the case that the processor applies two or more of the predetermined modifications to a region, the processor chooses the ratio of the predetermined modifications to apply to the region. The processor may apply a weighted combination of two or more of the predetermined modifications to the region. For example, the processor may store three predetermined modifications: modification 1, modification 2 and modification 3. Based on the image properties of the regions in the image, the processor may choose to apply: a region-specific modification to region 1 which is composed of 5% modification 1, 10% modification 2 and 85% modification 3; and a region-specific modification to region 2 which is composed of 80% modification 1, 15% modification 2 and 5% modification 3.

Applying predetermined modifications reduces the latency of correcting the video stream since the modifications themselves do not need to be generated on the fly, only the proportions of those modifications to apply. The predetermined modifications may be generated with knowledge of the typical image properties of images from the surgical site. For example, the known limited colour channels, high contrast, highly reflective portions etc. The predetermined modifications may also be generated with knowledge of the typical features in images from the surgical site. For example, a predetermined modification may be generated for each one of a set of organs and tissue structures. For example, kidneys have a purple hue, thus a predetermined modification may be generated for a kidney which is different to a predetermined modification for an artery which has a strong red colour.

As mentioned above, the surgical endoscope may be a 3D surgical endoscope having two offset channels. In this case, the processor applies a mask to each video channel. The images received from the two channels are offset, and hence the mask applied to one video channel is offset from the mask applied to the other video channel. The masks are offset such that the perceived image viewed by the surgeon has improved visibility compared to the uncorrected video stream.

When the mask is modified for a predicted relationship between features at the time of a subsequent image in the frame, the modification could be to change the region-specific modification of a region. For example, if a region is expected to become lighter as a result of a movement or a change of shape by the time of the subsequent image, then the region-specific modification may be altered to decrease the contrast and/or brightness compared to the previous region-specific modification.

As described above, the processor identifies a plurality of regions in an image. The processor analyses the image in order to select the regions. Each region may be a collection of pixels, each of which adjoins at least one other pixel in that region. The processor may group together pixels to form a region based on those pixels having similar values for any one or more of the following image properties: brightness, contrast, gamma, colour, saturation.

The processor may group together pixels to form a region based on feature identification in the image from data derived from the surgical robotic system. For example, organs and/or tissue structures can be identified in the image, either by automated image analysis or by the surgeon identifying the feature at some point during the surgical procedure. The processor may identify each of those organs and/or tissue structures to be a separate region. The processor may implement known edge finding techniques to determine the outline of the organ/tissue structure and hence the boundary of the region. This edge finding technique may be a coarse estimate which is not computationally intense. This is sufficient to enable the image correction method to improve the perceived visibility of the image, even if the boundary of the region does not perfectly match the outline of the organ/tissue structure.

The processor may group together pixels to from a region based on tracking the surgeon's focus. A first region may be selected to be an area of the image centred on the surgeon's focus. One or more further region may be selected to incorporate the remaining area of the image excluding the first region. Different region-specific modifications are applied to the first region and the further regions. To improve the image quality perceived by the surgeon but bearing in mind the need to reduce latency, a more computationally complex image correction process may be implemented on the first region, whilst a less computationally complex image correction process is implemented on the further regions. For example, the mask for the first region may be updated more frequently than the mask(s) for the further regions.

The processor may use predetermined image regions in order to select the regions of the image. The predetermined image regions may include, for example, an inner region and an outer region of the image. The processor may generate regions based on these predetermined image regions, but modify those regions based on any of the methods described above. For example, the processor may store predetermined inner and outer regions of the image. The processor may also track the surgeon's focus. If that focus moves from the centre of the screen, then the processor may modify the regions so as to cause the centre of the inner region to shift to the point of the surgeon's focus. As another example, the processor may store predetermined inner and outer regions of the image. The processor may also tag and track organs/tissue structures. If a tagged organ is mostly located in the inner region of the image but partly extends into the outer region, the processor may modify the inner region to encompass the whole of the tagged organ.

The processor may modify the regions for a subsequent image. This may be based on the predicted relationship between features of the image at the time of the subsequent image. For example, the processor may predict that the relationship between the features will change because the surgical endoscope is moving towards a feature, so that feature will occupy a larger proportion of the image. If the processor had identified that feature as being a region, then that region would become larger, i.e. be a larger set of pixels, in the subsequent image. By tracking the surgical endoscope, the surgical instrument(s) and tagging and tracking features in the image, the processor can identify changes to the regions and modify the regions for subsequent images to allow for the changing relationship between the features in the image. The modified mask for the subsequent image would then be applied to the modified regions of the subsequent image.

Image correction of the video stream is performed in real-time in order to enable the surgeon to see the surgical site that he is operating in. In order to enable the processor to perform the image correction described with sufficiently low latency that the surgeon does not perceive a delay between his moving an instrument at the surgical site and viewing that movement on the display, one or more of the following measures may be implemented. The mask may be applied using a low latency image processing pipeline. The same mask may be applied to a series of images, as described with respect to FIG. 4. In this case, the mask is updated more slowly than the image frame rate. The mask may be updated at regular intervals. For example, the mask may be updated once every 10 frames. Alternatively, or in addition, the mask may be updated when triggered by a certain action of a component of the surgical robotic system. To further reduce latency, the mask may be updated only when triggered by such an action. This action may be a gross change of the features in the image. A gross change of the features in the image may result from a gross movement of the surgical endoscope. A gross change of the features in the image may result from a gross movement of the patient's body, for example as a result of tilting the patient. These gross changes may be determined from image analysis or may be derived from the surgical robotic system itself. The mask may be updated in response to the position and/or orientation of the surgical endoscope within the patient. The mask may be updated in response to features viewed in the 3D image received from the surgical endoscope.

The masks described above provide an improved method of real-time image correction of a video stream from a surgical endoscope. In addition to using a mask generated as described above, a more accurate mask may be manually generated for a specific image and applied to the video stream when available. Such a mask is generated more slowly than the real-time mask generation described herein. Thus, the update rate of masks created in this manner will be lower than for the masks described herein.

The real-time image correction method described herein could be used for purposes other than correcting the video stream of a surgical endoscope of a surgical robotic system during a surgical procedure. For example, the method could be used for correcting the video stream from an endoscope of a robot used in car manufacturing for viewing the inside of an engine.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A method of real-time image correction of a video stream from a surgical endoscope of a surgical robotic system, the video stream comprising a sequence of images, the method comprising:
    for an image in the sequence of images, identifying a plurality of regions, each region having a different range of values of at least one image property to another region;
    applying a mask to the image which applies a region-specific modification to each region, each region-specific modification modifying the at least one image property of that region;
    deriving data from the surgical robotic system;
    determining a relationship between features in the image from the derived data;
    modifying the mask for a predicted relationship between the features at the time of a subsequent image in the video stream; and
    applying the modified mask to the subsequent image in the video stream.

2. The method of claim 1, further comprising storing a set of predetermined modifications, and generating each region-specific modification as a weighted combination of two or more predetermined modifications.

3. The method of claim 2, wherein the predetermined modifications modify one or more of the following image properties: brightness, contrast, gamma and colour.

4. The method of claim 1, wherein the predicted relationship between the features at the time of the subsequent image is such that the shape of one or more of the features in the image has changed.

5. The method of claim 1, wherein the predicted relationship between the features at the time of the subsequent image is such that the relative positions of the features have changed.

6. The method of claim 1, wherein the data comprises the position of the surgical endoscope relative to another feature in the image.

7. The method of claim 1, wherein the data comprises depth information of the features in the image.

8. The method of claim 7, comprising deriving the depth information from movement of the surgical endoscope.

9. The method of claim 7, wherein the video stream is a combination of two stereo video channels of the surgical endoscope, the method comprising deriving the depth information from the two stereo video channels of the surgical endoscope.

10. The method of claim 1, wherein the data comprises identification of features in the image.

11. The method of claim 1, comprising tracking the surgeon's focus, selecting a first region of the image to be centred on the surgeon's focus, selecting a second region of the image to exclude the surgeon's focus, and applying different region-specific modifications to the first and second regions.

12. The method of claim 10, comprising selecting regions of the image to correspond to identified features of the image, and applying feature-specific modifications to those selected regions.

13. The method of claim 1, comprising identifying a plurality of regions of the subsequent image based on the predicted relationship between the features at the time of the subsequent image in the video stream, wherein applying the modified mask to the subsequent image in the video stream comprises applying a region-specific modification to each region of the subsequent image.

14. The method of claim 1, further comprising applying an iteratively updated mask to further images of the video stream by:
    deriving further data from the surgical robotic system;
    determining an updated relationship between features in a further image of the sequence of images from the derived further data;
    further modifying the mask to form an updated mask for the updated predicted relationship between the features at the time of a yet further image in the video stream;
    applying the updated mask to the yet further image in the video stream; and
    iteratively performing the above steps for further images of the video stream.

15. The method of claim 14, comprising updating the mask at a slower rate than the image frame rate of the video stream.

16. The method of claim 14, comprising only updating the mask upon gross changes of the features in the image.

17. The method of claim 16, comprising only updating the mask upon gross movement of the surgical endoscope and/or the patient the surgical endoscope is inside.

* * * * *